United States Patent [19]
Osborn, III et al.

[11] Patent Number: 5,885,265
[45] Date of Patent: Mar. 23, 1999

[54] WATER DISPERSIBLE AND FLUSHABLE INTERLABIAL ABSORBENT STRUCTURE

[75] Inventors: Thomas Ward Osborn, III; Nicholas Albert Ahr, both of Cincinnati, Ohio

[73] Assignee: The Procter & Gamble Company, Cincinnati, Ohio

[21] Appl. No.: 706,371

[22] Filed: Aug. 30, 1996

Related U.S. Application Data

[63] Continuation-in-part of Ser. No. 561,989, Nov. 22, 1995, Pat. No. 5,722,966.

[51] Int. Cl.⁶ .................................................. A61F 13/15
[52] U.S. Cl. ........................................ 604/367; 604/385.1
[58] Field of Search .................................. 604/364–367, 604/385.1, 387

[56] References Cited

U.S. PATENT DOCUMENTS

| | | |
|---|---|---|
| 3,078,849 | 2/1963 | Morse . |
| 3,407,814 | 10/1968 | George et al. . |
| 3,510,587 | 5/1970 | Marder et al. . |
| 3,542,028 | 11/1970 | Beebe et al. . |
| 3,561,447 | 2/1971 | Alexander . |
| 3,636,952 | 1/1972 | George . |
| 3,665,923 | 5/1972 | Champaigne, Jr. . |
| 3,683,919 | 8/1972 | Ells . |
| 3,881,987 | 5/1975 | Benz . |
| 3,911,173 | 10/1975 | Sprague, Jr. . |
| 3,950,578 | 4/1976 | Laumann . |
| 3,967,623 | 7/1976 | Butterworth et al. . |
| 4,057,061 | 11/1977 | Ishikawa et al. . |
| 4,321,924 | 3/1982 | Ahr . |
| 4,425,130 | 1/1984 | DesMarais . |
| 4,514,345 | 4/1985 | Johnson et al. . |
| 4,608,047 | 8/1986 | Mattingly . |
| 4,610,678 | 9/1986 | Weisman et al. . |
| 4,687,478 | 8/1987 | Van Tilburg . |
| 4,690,680 | 9/1987 | Higgins . |
| 4,785,996 | 11/1988 | Ziecker et al. . |
| 4,830,187 | 5/1989 | Keyes et al. . |
| 4,834,735 | 5/1989 | Alemany et al. . |
| 4,842,666 | 6/1989 | Werenicz . |
| 4,917,697 | 4/1990 | Osborn, III et al. . |
| 4,950,264 | 8/1990 | Osborn, III . |
| 5,026,363 | 6/1991 | Pratt . |
| 5,058,247 | 10/1991 | Thomas et al. . |
| 5,116,563 | 5/1992 | Thomas et al. . |
| 5,147,345 | 9/1992 | Young et al. . |
| 5,190,533 | 3/1993 | Blackburn . |
| 5,207,662 | 5/1993 | James . |
| 5,230,851 | 7/1993 | Thomas . |
| 5,245,025 | 9/1993 | Trokhan et al. . |
| 5,300,358 | 4/1994 | Evers . |
| 5,384,189 | 1/1995 | Kuroda et al. . |

(List continued on next page.)

FOREIGN PATENT DOCUMENTS

| | | |
|---|---|---|
| 0 198 683 A2 | 10/1986 | European Pat. Off. . |
| 0 605 016 A2 | 7/1994 | European Pat. Off. . |
| 282447 | 5/1928 | United Kingdom . |
| WO 95/03361 | 3/1994 | WIPO . |
| WO 95/16474 | 12/1994 | WIPO . |

*Primary Examiner*—Robert A. Clarke
*Attorney, Agent, or Firm*—Edward J. Milbrada; Jeffrey V. Bamber; Steven W. Miller

[57] ABSTRACT

A flushable and dispersible interlabial absorbent structure having a liquid pervious topsheet, a liquid impervious backsheet and an absorbent core is described. The topsheet is preferably a wet laid, apertured fibrous web having a temporary wet strength resin incorporated therein. The body surface of the topsheet also has a plurality of fibrils, the fibrils are made of a water resistant resinous material. The backsheet is preferably a wet laid fibrous assembly having a temporary wet strength resin incorporated therein. The body surface of the backsheet is also preferably coated with a water resistant resinous material. The absorbent core is positioned between the topsheet and the backsheet. The topsheet and the backsheet are joined, at least about their periphery, using a water soluble adhesive. The interlabial absorbent structure also may have means for removably attaching the interlabial absorbent structure to the interior surfaces of a wearer's labia.

22 Claims, 5 Drawing Sheets

U.S. PATENT DOCUMENTS

| | | | |
|---|---|---|---|
| 5,397,316 | 3/1995 | LaVon et al. | 604/385.1 |
| 5,405,342 | 4/1995 | Roessler et al. . | |
| 5,415,643 | 5/1995 | Kolb . | |
| 5,443,691 | 8/1995 | Phan et al. . | |
| 5,476,457 | 12/1995 | Roessler et al. . | |
| 5,573,523 | 11/1996 | Whalen et al. . | |
| 5,599,339 | 2/1997 | Horney | 604/387 |
| 5,618,282 | 4/1997 | Schlangen | 604/387 |
| 5,722,966 | 3/1998 | Christon et al. | 604/364 |
| B1 4,589,876 | 4/1993 | Van Tilburg . | |

WATER DISPERSIBLE AND FLUSHABLE INTERLABIAL ABSORBENT STRUCTURE

This is a continuation-in-part of U.S. patent application Ser. No. 08/561,989, filed on Nov. 22, 1995, U.S. Pat. No. 5,722,966.

FIELD OF THE INVENTION

The present invention is directed to absorbent articles such as catamenial devices, incontinence pads, or the like. More particularly, the present invention is directed to interlabial absorbent structures that may be disposed of during the flush cycle of a conventional toilet without causing disposal problems thereby.

BACKGROUND OF THE INVENTION

Disposable absorbent articles have been commercially available for many years and have met with great success world wide. For example, continuing improvements to catamenial devices have freed women from much of the inconvenience of their monthly menstrual period. However, further improvements are still needed.

One class of catamenial device, interlabial pads, has the potential to provide even greater freedom from inconvenience because of the discretion provided by their small size and reduced risk of leakage. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. Nos. 5,074,855 and 5,336,208 issued to Rosenbluth, et al. on Dec. 24, 1991 and Aug. 9, 1994 respectively, and U.S. Pat. No. 5,484,429 issued to Vukos, et al. on Jan. 16, 1996. A commercially available interlabial device is Fresh 'n Fit® Padette which is marketed by ATHENA Medical Corp. of Portland, Oreg. and described in U.S. Pat. Nos. 3,983,873 and 4,175,561 issued to Hirschman on Oct. 5, 1976 and Nov. 27, 1979 respectively. While the Fresh 'n Fit® Padette has enjoyed some commercial success, such interlabial devices lack a barrier to prevent absorbed bodily fluids from passing through the device and staining a wearer's undergarments or other clothing.

In the past a number of attempts have been made to provide flushable absorbent articles. British Patent No. 282,447 attempts a partial solution by providing a core said to be flushable and a repellent treated barrier which is separated from the core and needs to be disposed of by other means. U.S. Pat. No. 3,078,849, issued to Morse on Feb. 26, 1962, describes a sanitary napkin incorporating a fluid sensitive, temporary barrier within the absorbent core for spreading bodily fluids but makes no provision for a water sensitive outer covering. U.S. Pat. No. 3,561,447, issued to Alexander on Mar. 13, 1969, describes a sanitary napkin having a nonwoven fabric covering wherein the nonwoven fabric comprises textile length fibers and the binder for the nonwoven is a combination of a soft acrylic binder and polyvinyl alcohol. This combination is said to have sufficient strength when damp to serve as an outer covering while still dispersing in water when exposed to mild agitation. While such a structure may have limited wet strength, it is unlikely that it will have sufficient barrier properties to be a satisfactory backsheet for a modern sanitary napkin. U.S. Pat. No. 3,665,923, issued to Champaigne, Jr. on May 30, 1972, describes a sanitary napkin with an wrapper comprising a nonwoven fiber web that is bonded by a water dispersible adhesive such as poly (vinyl alcohol). A preferred embodiment also comprises a baffle member of a thin impervious plastic film interposed between the absorbent pad and the wrapper. This structure solves the problem of providing barrier properties by providing a non dispersible member with the requisite barrier properties. Repeated flushing of such structures poses the risk of clogging sewer pipes because the baffle member will not disperse into small particles in a toilet. U.S. Pat. No. 5,300,358, issued to Evers on Apr. 5, 1994 describes absorbent structures wherein the backsheet comprises two sheets of poly (vinyl alcohol) film with a highly absorbent paper structure therebetween. All surfaces that may be exposed to aqueous fluids are treated with a water repellent material, such as a fluorocarbon. The absorbent structure is also provided with a tear strip or string which, when pulled at disposal, is said to expose the highly absorbent paper structure to water which then wicks the water to the non repellent treated surfaces so they can dissolve. The requirement of a tear strip is an obvious inconvenience.

Thus, it is an object of the present invention to provide an interlabial absorbent structure with performance properties (such as wearer comfort, leakage resistance, and the like) equaling or exceeding those of contemporary interlabial devices. It a further object of the present invention to provide interlabial absorbent structures that provide improved convenience and discretion when the used interlabial absorbent structure is disposed of. It is still a further object of the present invention to provide an interlabial absorbent structure that may be disposed of by flushing the article down a conventional toilet wherein the interlabial absorbent structure readily disperses into portions sufficiently small so as not to clog plumbing when the used interlabial absorbent structure is flushed.

SUMMARY OF THE INVENTION

The present invention provides an absorbent article, such as an interlabial absorbent structure, that disperses into fragments which are readily flushable in a normal toilet. The preferred interlabial absorbent structure of the present invention comprises a liquid pervious topsheet, a backsheet impervious to bodily fluids, and an absorbent core positioned between the topsheet and the backsheet. An alternative embodiment also comprises means for removably attaching the device to a wearer's body.

The preferred liquid pervious topsheet of the present invention comprises a wet laid apertured tissue having a temporary wet strength resin incorporated therein. Portions of the body surface of the tissue are further provided with a resinous material. Preferably, the resinous material comprises a water resistant resinous material that is provided in the form of fibrils printed on the body surface of the topsheet. Alternatively, the resinous material can provide the topsheet with a surface energy gradient between the body surface thereof and the garment surface thereof. The preferred topsheet of the present invention acquires bodily fluids at an excellent rate and is soft and comfortable to wear.

The preferred backsheet of the present invention comprises a wet laid fibrous assembly having a temporary wet strength resin incorporated therein. The backsheet is further coated with a water resistant resinous material that causes the backsheet to become impervious to bodily fluids without impairing the spreading of adhesive materials thereon.

Backsheets of the type described herein represent an improvement over those described in the art in that flushable absorbent articles of the prior art typically use materials having a very low critical surface tension to help ensure the backsheet would be impervious with resulting difficulty in adhesively joining such backsheets to the remaining components of a sanitary napkin. The backsheet of the present invention presents no such joinder issues.

The interlabial absorbent structure is assembled by disposing the backsheet such that a surface thereof that is coated with a water resistant resinous material is oriented toward the core. The core and the topsheet are disposed thereon, and the components joined using means known to those skilled in the art. A water soluble adhesive is used to join the components of the preferred interlabial absorbent structure of the present invention in at least an area of peripheral bonding so the components will separate when the interlabial absorbent structure is exposed to water in a toilet.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad. A preferred embodiment of a unitary disposable absorbent article of the present invention is the interlabial absorbent structure 20 shown in FIG. 1. As used herein, the term "interlabial absorbent structure" describes an absorbent article which resides at least partially between a wearer's labia and which is intended to absorb and contain menstrual fluids and other discharges from the wearer's body (e.g., blood and urine). Such interlabial absorbent structures are suitable for use as catamenial devices for women who have reached their menarche but not yet reached menopause and as incontinence pads, and the like for female wearers. As used herein, the term "pudendal" refers to the externally visible female genitalia.

General Description of the Interlabial Device of the Present Invention

Figure 1:
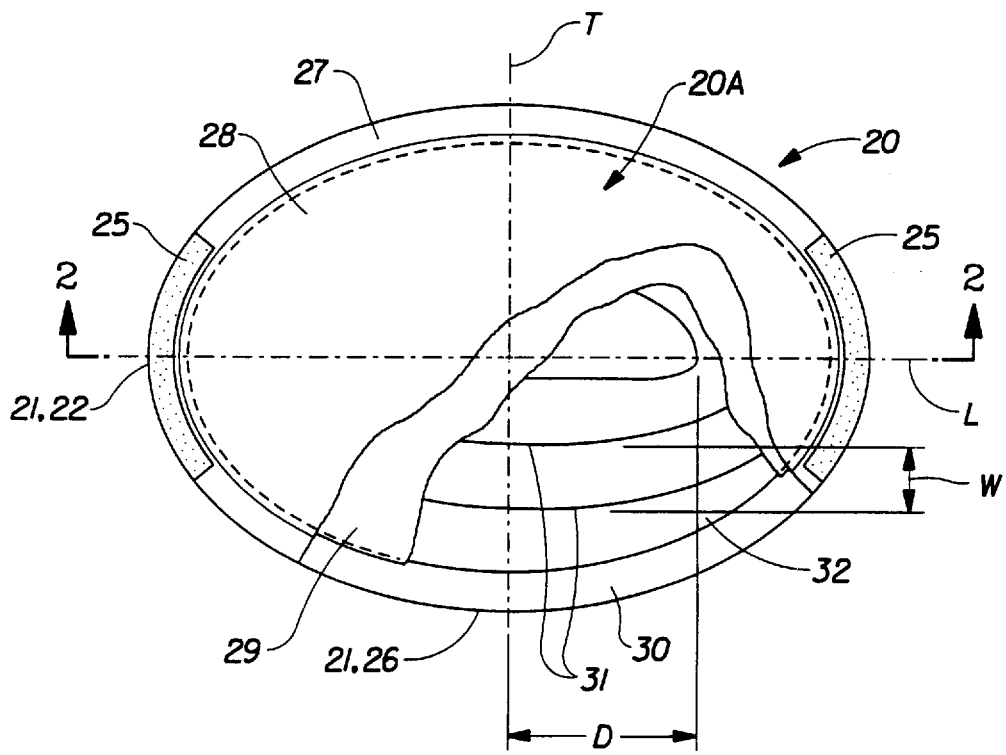
FIG. 1 is a top plan view of a preferred interlabial absorbent structure embodiment of the present invention shown partially cutaway to show the underlying structure.

FIG. 1 is a top plan view of the interlabial absorbent structure 20 of the present invention in its flat-out state with portions of the structure being cut-away to more clearly show the construction of the interlabial absorbent structure 20 and with the portion of the interlabial absorbent structure 20 which faces or contacts the wearer, oriented towards the viewer. As shown in FIG. 1, the interlabial absorbent structure 20 preferably comprises a liquid pervious topsheet 28, a liquid impervious backsheet 30 joined with the topsheet 28, and an absorbent core 32 positioned between the topsheet 28 and the backsheet 30.

The interlabial absorbent structure 20 has two surfaces, a body-contacting surface or "body surface" 20A and a garment surface 20B. In a similar manner each component comprising the interlabial absorbent structure 20 may have a body surface designated by the reference number for the component with an appended A and a garment surface designated by the reference number for the component and an appended B. The interlabial absorbent structure 20 is shown in FIG. 1 as viewed from its body surface. The body surface 20A is intended to be worn adjacent to the body of the wearer while the garment surface 20B is on the opposite side and is intended to be oriented away from the surface contacting a wearer's body when the interlabial absorbent structure 20 is worn. The interlabial absorbent structure 20 also has a longitudinal centerline L and a transverse centerline T. The term "longitudinal", as used herein, refers to a line, axis or direction in the plane of the interlabial absorbent structure 20 that is generally aligned with (e.g., approximately parallel to) a vertical plane which bisects a standing wearer into left and right body halves when the interlabial absorbent structure 20 is worn. The terms "transverse" or "lateral" as used herein are interchangeable and refer to a line, axis, or direction within the plane of the interlabial absorbent structure 20 that is generally perpendicular to the longitudinal direction.

The interlabial absorbent structure 20 can be of any suitable size and shape that allows at least a portion thereof to fit comfortably within the wearer's labia minora and to cover the wearer's vaginal introitus, and preferably at least partially cover the wearer's urethra. The interlabial absorbent structure 20 at least partially blocks and, more preferably, completely blocks and interrupts the flow of menses, urine, and other bodily exudates from the wearer's vaginal introitus and urethra. The interlabial absorbent structure 20 is preferably provided with sufficient absorbency to absorb and retain these exudates. The interlabial absorbent structure 20 is preferably at least partially retained in place by exerting a slight outwardly-oriented pressure on the inner surface of the wearer's labia.

Although shapes (when viewed in top plan view), such as rectangular, rounded rectangular, or rounded triangular are also suitable, the preferred embodiment of the interlabial absorbent structure 20 has a generally oval plan view as is shown in FIG. 1. The interlabial absorbent structure 20 also has end edges 22 and a pair of longitudinal side edges (or lateral edges) 26. FIG. 1 also shows that the interlabial absorbent structure 20 has a periphery 21 which is defined by the end edges 22 and the longitudinal side edges 26. Although other dimensions may be suitable for specific needs, the interlabial absorbent structure 20 preferably measures about 4.5 inches (about 11.4 cm.) in length, and about 3.5 inches (about 8.9 cm) in width. The caliper of the interlabial absorbent structure 20 shown in FIGS. 1–3 is preferably less than about 4 mm measured under a pressure of 0.25 psi (1.7 kPa).

Figure 6:
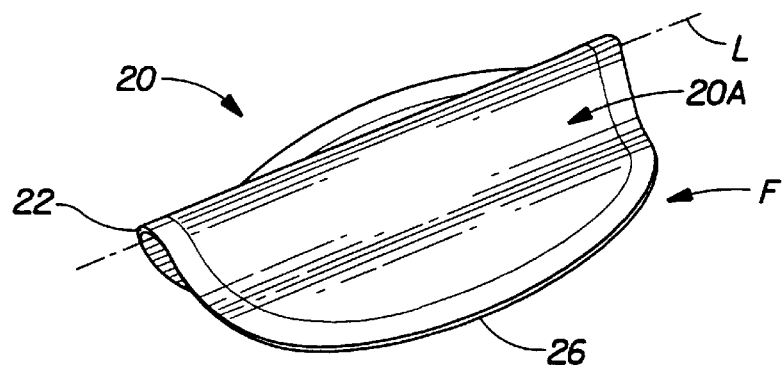
FIG. 6 is a perspective view of an interlabial absorbent structure of the present invention in a folded configuration.

The interlabial absorbent structure 20 shown in FIG. 1 is initially relatively flat and then is folded into the desired shape for insertion into the space between the wearer's labia minora as shown in FIG. 6. In alternative embodiments, the interlabial absorbent structure 20 could be provided in a shape that closely conforms to the shape of the space between the inside surfaces of the wearer's labia minora without any folding or other manipulation by the wearer. For example, the interlabial absorbent structure 20 of the present invention could be provided with a cylindrical shape.

Figure 2:
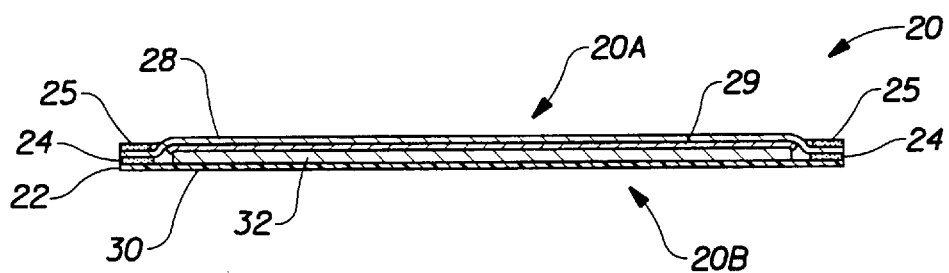
FIG. 2 is an enlarged cross-sectional view of the preferred interlabial absorbent structure embodiment shown in FIG. 1 taken along line 2—2 of FIG. 1.
Figure 3:
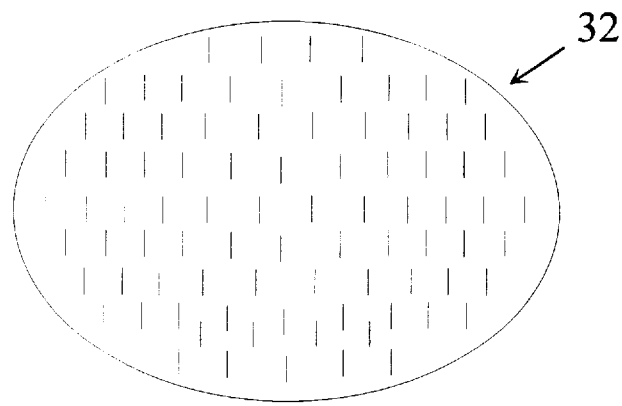
FIG. 3 is a plan view of an alternative slit pattern for the absorbent core of the present invention.

FIG. 2 shows the individual components of the interlabial absorbent structure 20. The interlabial absorbent structure 20 shown in FIG. 1 preferably comprises at least three primary components: a liquid pervious topsheet 28; a liquid impervious backsheet 30 that is joined to the topsheet; and an absorbent core 32 positioned between the topsheet and the backsheet. The topsheet 28 also may comprise a secondary topsheet layer that forms the underside (or core-facing side) of the topsheet 28. Such a secondary topsheet layer is shown as 29 in FIG. 2 and discussed in the Optional Components section below. A second optional component is a body adhesive 25 that may be disposed on portions of the body surface 20A of the interlabial absorbent structure 20. The components of the interlabial absorbent structure 20 can be comprised of a number of suitable materials such materials are discussed in detail with respect to the individual components below.

The interlabial absorbent structure 20 of the present invention is flushable. As used herein the terms "flushable and flushability" are defined as a product's ability to pass through typical commercially available household toilets and plumbing drainage systems without causing clogging or similar problems that can be directly associated with the physical structure of the product. Typically, such clogs occur at bends in such plumbing systems or at intrusions, such as roots, into the plumbing system. The following model relates product properties to clogging potential.

Clogging Potential=F (probability of interacting with a bend or intrusion, probability of attaching to the bend or intrusion)

Among other factors, the first probability depends on: 1) the size of the product or product portions passing through the plumbing system; 2) the area of the product or product portions that is perpendicular to the flow direction; and 3) the flexibility of the product or product portions passing through the plumbing system; and the second probability depends on 1) the mechanical strength of the product or product portions; and 2) the "stickiness" of the product or product portions. As will be discussed below, this model can be used to identify preferred designs and materials for a flushable, interlabial absorbent structure.

The Absorbent Core

The absorbent core 32 may be any absorbent means which is capable of absorbing or retaining liquids (e.g., menses and/or urine). As shown in FIGS. 1 and 2, the absorbent core 32 has a body surface, a garment surface, side edges, and end edges. The absorbent core 32 may be manufactured in a wide variety of sizes and shapes (e.g., rounded rectangular, oval, etc.) and from a wide variety of liquidabsorbent materials commonly used in interlabial absorbent structures and other absorbent articles such as comminuted wood pulp which is generally referred to as airfelt. Examples of other suitable absorbent materials include creped cellulose wadding; melt-blown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers, both in fibrous form and in particulate form; absorbent gelling materials; or any equivalent material or combinations of materials, or mixtures of these. The configuration and construction of the absorbent core may also be varied (e.g., the absorbent core may have varying caliper zones (e.g., profiled so as to more closely conform to the space between the inside surfaces of a wearer's labia minora), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the interlabial absorbent structure. Further, the size and absorbent capacity of the absorbent core may be varied to provide interlabial absorbent structures having a capacity appropriate for an intended use.

The absorbent core 32 is preferably provided with a continuous cut 31 in the form of a spiral pattern. Such a pattern not only softens the absorbent core 32 but also permits the absorbent core to assume a three dimensional configuration whereby the interlabial absorbent structure 20 is better able to conform to a wearer's body. As can be seen in FIG. 1, the cut 31 has a spiral form which is initiated adjacent the intersection of the longitudinal centerline L and the transverse centerline T. Cut 31 runs parallel longitudinal centerline L for a longitudinal distance D before curving. As can also be seen in FIG. 1, the spacing between the segments of the cut 31 divides the absorbent core 32 into core segments having a width W. By controlling the relative size of the longitudinal distance D and the segment width W, the flexibility and the degree of response of the absorbent core 32 to bodily movement can be varied. Specifically, as longitudinal distance D increases, the absorbent core 32 bends more readily about the longitudinal centerline L and as width W decreases, the absorbent core 32 becomes softer and more readily conforms to a wearer's body. Conversely, if dimension D becomes too long or dimension W becomes too small, the absorbent core 32 will lose mechanical integrity during use. A longitudinal length D, expressed as a percentage of the longitudinal length of the interlabial absorbent structure 20, of between about 15% and about 85% has been found to be suitable. Preferably, the longitudinal length D is between about 20% and about 70% and more preferably between about 25% and about 50%. A segment width W between about 0.2 inch (0.5 cm) and about 0.75 inch (1.9 cm) has been found to provide a satisfactory balance of softness and mechanical strength. Preferably, the segment width W is between about 0.3 inch (0.8 cm) and about 0.6 inch (1.5 cm) and more preferably about 0.4 inch (1 cm).

While the spiral cut 31 provides a preferred balance of flexibility and core mechanical strength (see below), the absorbent core 32 can be provided with slits or cuts having other suitable configurations. For example, the absorbent core can be provided with a plurality of transversely-oriented slits that are arranged in rows. Preferably, the slits in adjacent rows are staggered so that the absorbent core 32 will be extensible in the longitudinal direction. Such extensibility both softens the absorbent core 32 and allows it to extend in the longitudinal direction. An absorbent core having such a slit pattern is shown in FIG. 3.

Additionally, any type of cuts or slits that may be provided to the absorbent core 32 create lines of weakness therein which more readily enable the absorbent core 32 to break up into smaller pieces due to the forces encountered when the interlabial absorbent structure 20 is disposed of by flushing it down a toilet (e.g. forces due to water turbulence or drag forces from moving water if the absorbent core 32 is temporarily "hung up" on a snag that may have intruded into the plumbing system). Such smaller pieces will flow through plumbing systems with reduced risk of causing the formation of clogs therein (i.e. the probability of interacting with the plumbing system goes down). For example, the effect of providing such slits and cuts can be demonstrated by the following experiment. Table 1 below compares the wet trouser tear strength of two similar structures suitable for use as an absorbent core 32. The only difference in the structures is that one of the structures has been provided with slits having the pattern shown in FIG. 3 (One of ordinary skill in the art would recognize that, while the preferred spiral cut 31 shown in FIG. 1 would provide a reduction in mechanical strength to the core 32 similar to that provided by the pattern of FIG. 3 because both patterns provide lines of weakness, the slit pattern of FIG. 3 will provide a more reliable sample for quantitative determination of the effect of such slits on the strength of a core 32.).

TABLE 1

| | Absorbent Core No Cut | Configuration Cut |
|---|---|---|
| Wet Trouser Tear Strength (Grams) 5 minutes after spraying with water | 73 | 35 |

Trouser tear strength simulates the difficulty of tearing absorbent core 32 if it might snag on an obstruction in a plumbing system. As can be seen in Table 1, providing the slits or cuts substantially reduces (by more than 50%) the difficulty of breaking up the absorbent core 32 into smaller pieces when it is wet. A method for measuring the wet trouser tear strength of an absorbent core 32 is provided in the TEST METHODS section below. Absorbent cores 32 having a wet trouser tear strength of less than about 60 grams have been found to be suitable for the present invention. Preferably, the absorbent core 32 has a wet trouser tear strength of less than about 50 grams, more preferably, less than about 40 grams.

Exemplary absorbent structures for use as the absorbent core 32 of the present invention are generally described in U.S. Pat. No. 4,950,264, issued to Osborn on Aug. 21, 1990; U.S. Pat. No. 4,610,678, issued to Weisman et al. on Sep. 9, 1986; U.S. Pat. No. 4,834,735, issued to Alemany et al. on May 30, 1989; and European Patent Application No. 0 198 683, The Procter & Gamble Company, published Oct. 22, 1986 in the name of Duenk, et al. The disclosure of each of these patents and published applications is incorporated herein by reference. High internal phase emulsion (HIPE) foams as are described in U.S. Pat. No. 5,147,345 issued to Young, et al. on Sep. 15, 1992 also provide suitable absorbent structures for the present invention.

A preferred embodiment of the absorbent core 32 has the same general shape as the interlabial absorbent structure 20 and comprises a blend of comminuted wood pulp and thermoplastic binder fibers. Such blends are deposited on a screen using well know air laying methods to form a web and heated air is blown through the web to melt the thermoplastic binder and bond the fibers to form a mechanically stable assembly. A wood pulp suitable for comminution is provided by the Buckeye Cellulose Corp. of Memphis, Tenn. under the designation Foley Fluff. A suitable thermoplastic binder fiber is PLEXAFIL® polyethylene microfibers (made by DuPont, Wilmington, Del.). Such structures are described more fully in U.S. Pat. application Ser. No. 08/141,156 filed on Oct. 21, 1993 in the name of Richards, et al. (allowed, no number assigned; published as PCT Application No. WO 95/10996), the disclosure of which is incorporated herein by reference. A particularly preferred blend of such fibers comprises between about 70% and 90% wood pulp fibers and between about 30% and 10% thermoplastic binder fibers. More preferably the blend of fibers comprises about 80% wood pulp fibers and about 20% thermoplastic binder fibers.

Additionally, fibrous or particulate superabsorbent polymers may optionally be included in the blend. A suitable particulate superabsorbent polymer is provided by Nalco Chemical Co. of Naperville, Ill. under the designation Nalco 1180.

The Backsheet

The backsheet 30 acts as a barrier to any absorbed bodily fluids that may pass through the absorbent core 32 to the garment surface 32B thereof with a resulting reduction in risk of staining undergarments or other clothing. Further, the barrier properties of the backsheet 30 permit manual removal, if a wearer so desires, of the interlabial absorbent article 20 with reduced risk of hand soiling. The backsheet 30 is impervious to bodily fluids (e.g., menses and/or urine) yet readily dispersible in cold water under the mild agitation seen when flushing a conventional toilet. As used herein, a material is impervious to bodily fluids (i.e. "water resistant") if the material is capable of maintaining a hydrostatic head that is greater than about 12 cm without substantial leakage when evaluated using the method described in the TEST METHODS section below. The backsheet 30 is preferably manufactured from a wet laid tissue that also comprises a temporary wet strength resin. The tissue has also preferably been coated with a water resistant resinous material. Further, the backsheet 30 may permit vapors to escape from the absorbent core 32 (i.e., breathable) while still preventing exudates from passing through the backsheet 30.

The backsheet 30 is also, preferably, accorded a mechanical treatment to fully develop and enhance its softness and wearing comfort. This treatment can be applied effectively by differential working with resulting microcreping wherein the backsheet 30 is confined between a rubber belt at varying tensions and a pulley face to produce microcreping in a system similar to that disclosed in U.S. Pat. No. 2,624,245 issued to Cluett on Jan. 6, 1953 and popularly known as "Clupaking." An alternative treatment, popularly known as "Micrexing", is also suitable for mechanically working the backsheet 30. This treatment uses apparatus produced by the MICREX® Corp., Walpole, Mass. Such apparatus provides a web of material with controlled microcreping by supporting the web on rotating roll which introduces the web into a converging passage leading to a treatment cavity where the web is provided with microcrepes. Such a treatment is described in U.S. Pat. Nos. 3,260,778, 3,426,405, and 5,117,540, issued to Walton or Walton, et al. on Jul. 12, 1966, Feb. 11, 1969, and Jun. 2, 1992 respectively. The disclosure of which patents is incorporated herein by reference.

As noted above, a preferred fibrous assembly is a wet laid tissue having a wet strength resin incorporated therein. A suitable tissue has a basis weight of about 12 pounds per 3000 square feet and is available from Georgia-Pacific Corp. of Bellingham, Wash. under the designation DST-2. Also as noted above, the wet laid tissue is preferably coated with a water resistant resinous material to render it impermeable to bodily fluids. A suitable water resistant resinous material is a hot melt resin blend which is available from Century International of Columbus, Ohio under the designation CA-105. Preferably, the coating weight is between about 0.005 grams per square inch (8 grams per square meter) and about 0.075 grams per square inch (116 grams per square meter). More preferably, the coating weight is between about 0.015 grams per square inch (23 grams per square meter) and about 0.035 grams per square inch (54 grams per square meter).

While a coated, wet laid tissue is preferred for the present invention, any fibrous assembly that is impervious to bodily fluids (for example, by being provided with a suitable coating), yet readily dispersible in cold water under mild agitation is suitable. Thus, suitable materials include carded, air laid, or wet laid assemblies of hydrophilic fibers. Suitable fibers include, but are not limited to, natural fibers (e.g., wood or cotton fibers), synthetic fibers (e.g., polymeric fibers such as polyester, polypropylene, or polyethylene fibers) or a combination of natural and synthetic fibers. In order to ensure easy dispersibility, such fibers should be either intrinsically hydrophilic or treated to be hydrophilic. As used herein, the contact angle between water and the material surface is used to define its relative hydrophilicity. The contact angle is less than 90 degrees for a material to be considered to be a "hydrophilic" material. Methods of treating fibrous assemblies to render them hydrophilic are described in U.S. Pat. No. 4,950,254 issued to Osborn on Aug. 21, 1990, the disclosure of which is incorporated herein by reference.

As noted above, the fibrous assemblies described herein should be treated to ensure they are impervious to bodily fluids. While treating one surface of a fibrous assembly to make that surface impervious to bodily fluids will provide a suitable material for use as a backsheet 30, treating both surfaces with a water resistant resinous material is preferred. Such fibrous assemblies can be treated to be impervious to bodily fluids by a process using the method described in U.S. Pat. No. 5,558,344, issued in the name of Ahr, et al. on Nov. 26, 1996 (allowed, no number assigned), the disclosure of which is incorporated herein by reference.

When such a wet laid tissue is coated with a water resistant resinous material using the resin application process described above, the resulting coated web is impervious to bodily fluids. Specifically, the coated web is capable of maintaining a hydrostatic head of at least about 12 centimeters, preferably 15 centimeters, when tested as described in the TEST METHODS section. More preferably, the coated web is capable of maintaining a hydrostatic head of at least about 18 centimeters.

Not only are the coated webs of the present invention impervious to bodily fluids, they also rapidly lose mechanical integrity and dissociate into fragments on immersion in water. For example, when samples of such coated webs are evaluated for flushability using the method described in the TEST METHODS section, the coated web behaves substantially the same as a sample of a commercially available toilet tissue (CHARMIN®) used as a control. That is, the sample of the coated web of the present invention breaks up into smaller pieces that readily pass through the test apparatus with no substantially clogging.

Reduction in burst strength on exposure to water is one measure of the loss of mechanical integrity discussed above. Table 2 below shows burst strength data for a sample of the preferred backsheet 30 of the present invention.

TABLE 2

| Coated Fibrous Assembly No. | 1 |
| --- | --- |
| Fibrous Assembly Type | DST-2 |
| Resinous Coating Material | CA-105 |
| Coating Weight | 0.025 g/in$^2$ (3.9 mg/cm$^2$) |
| Burst Strength (Grams) | |
| Dry | 698 |
| Wet (20 Second Soak) | 322 |
| Wet Burst (20 Second)/Dry Burst | 0.46 |

As can be seen, the reduction in burst on exposure to water (forty-six percent of the dry value after 20 seconds) means that the backsheet 30 is sufficiently weakened that it will disperse into fragments under the mild agitation conditions encountered when a conventional toilet is flushed.

The Applicants believe that the backsheet 30 loses strength rapidly on exposure to water because the water is able to penetrate minute pin holes in the resinous coating. Once the water has penetrated the resinous coating, it causes the fibrous assembly to lose mechanical strength. While not being bound by theory, the following model uses differences in rheology and surface chemical properties to explain why the backsheet 30 is impervious to bodily fluids yet water is able to penetrate the pin holes in the resinous coating and rapidly cause a loss in tensile properties.

It is well known that a bodily fluid, such as menses, has a higher viscosity than water (i.e. about 7.5 mPa sec versus about 1 mPa sec). Since viscosity controls flow rate, the higher viscosity of menses means that menses will pass through a pinhole more slowly. As a result, the time required for enough menses to pass through the pinholes to cause a meaningful loss in tensile properties is longer than the wear time of the interlabial absorbent structure.

The surface tension of menses (greater than about 46 dynes/cm) is higher than the critical surface tension of the backsheet 30 (34 dynes/cm) so there is a surface chemical barrier to wetting of the backsheet by bodily fluids such as menses.

The solid components of menses (epithelial cells and blood platelets, for example) would tend to block pin holes.

In other words, a series of physical and chemical barriers combine and act to interfere with bodily fluids passing through coating of the backsheet 30 and weakening the backsheet while it is being worn. On the other hand, when the interlabial absorbent structure 20 is put into a toilet for disposal many of these barriers are overcome (e.g. the low viscosity of water allows more rapid passage through the pin holes) and the backsheet 30 can begin to disintegrate.

Using the preferred water resistant resinous material of the present invention represents an improvement over the hydrophobic materials typically used by prior art flushable catamenial devices to protect the water sensitive material comprising the backsheet (a typical prior art water sensitive material is poly (vinyl alcohol) and a typical prior art hydrophobic material is a fluorocarbon). Specifically, the hydrophobic materials used by prior art have very low critical surface tensions. For example, the critical surface tension of Teflon® is less than 20 dynes per centimeter (Adamson, A. W., *Physical Chemistry of Surfaces,* 1976, John Wiley & Sons, New York, page 354). The critical surface tension of other fluorocarbon treated surfaces is similar. This low critical surface tension means that assembly of an absorbent article will be made more difficult because a low critical surface tension interferes with adhesive bonding because adhesives will not spread on and adhere to such surfaces (Low critical surface tension is also the basis of commercially available anti-stain treatments because stains will not adhere to surfaces having a low critical surface tension). This means there is a need to either ensure that there is no fluorocarbon in areas of adhesive bonding (with the resulting manufacturing complexity of insuring adequate registration of those areas with the remaining components of a interlabial absorbent structure) or to treat any fluorocarbon surface in an area of adhesive bonding to increase the critical surface tension thereof. Conversely, a surface coated with the preferred water resistant resinous material of the present invention has a critical surface tension of greater than about 34 dynes per centimeter when measured using the modified TAPPI test method (T 698 pm-83) described in the TEST METHODS section below. Thus, ordinary manufacturing processes can be used to assemble a interlabial absorbent structure using the preferred backsheet of the present invention without the necessity of additional processing steps.

Thus, as described herein, a water resistant resinous material not only provides a fibrous assembly with a surface that is impervious to bodily fluids (i.e., capable of supporting a hydrostatic head of greater than about 12 cm) but also provides the coated web with a surface suitable for joining to other components using adhesive means (i.e., critical surface tension greater than about 34 dynes per centimeter).

As noted above, the preferred structure of the resinous coating (i.e. coating both sides of the wet laid fibrous assembly) results in minute pinholes in the resinous coating. While being resistant to passage of bodily fluids (also discussed above), such pinholes also provide the backsheet 30 with breathability. That is water vapor and other gaseous materials can pass through the backsheet 30 with a resulting improvement in comfort to the wearer.

The Topsheet

The topsheet 28 is compliant, soft feeling, and non-irritating to the wearer's skin. Further, the topsheet 28 is liquid pervious permitting liquids (e.g., menses and/or urine) to readily penetrate through its thickness. The topsheet should also be readily dispersible under the mild agitation conditions encountered when a conventional toilet is flushed. A suitable topsheet 28 may be manufactured from a wide range of materials such as air laid, wet laid, or carded nonwoven materials. Suitable materials can be comprised of natural fibers (e.g., wood or cotton fibers), synthetic fibers (e.g., polymeric fibers such as polyester, polypropylene, or polyethylene fibers) or from a combination of natural and synthetic fibers.

Figure 4:
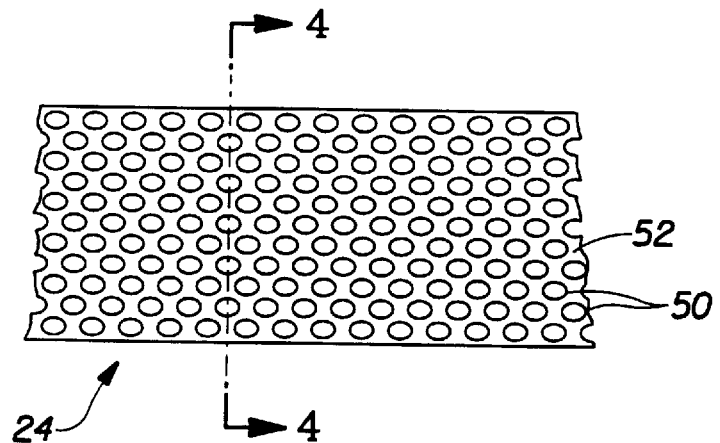
FIG. 4 is a plan view of the topsheet of the present invention.
Figure 5:
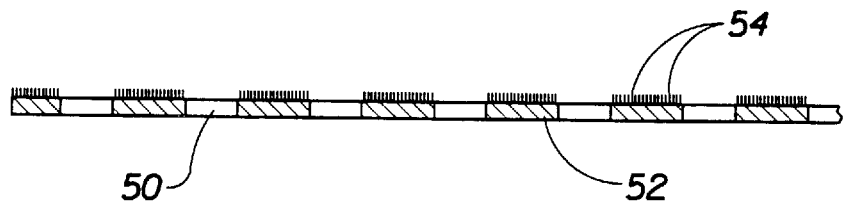
FIG. 5 is an enlarged cross-sectional view taken along line 4—4 of FIG. 4 showing the topsheet of the present invention.

A preferred topsheet 28 comprises a wet laid fibrous assembly, preferably, an apertured tissue having a temporary wet strength resin incorporated therein. A portion of such topsheet 28 is shown in FIGS. 4 and 5. As is shown in FIGS. 4 and 5, the preferred topsheet 28 comprises a wet laid fibrous assembly 52 having a multiplicity of apertures 50 therethrough. While a preferred fiber furnish for this tissue comprises cellulose fibers from wood, preferably about 90 percent Eucalyptus fibers and about 10% Northern Sulfite Kraft fibers, other fibrous materials, including but not limited to natural fibers (e.g., other types of wood fibers or cotton fibers), synthetic fibers (e.g., polymeric fibers such as polyester, polypropylene, or polyethylene fibers) or a combination of natural and synthetic fibers are also suitable as long as the fibers are, or can be treated to become, hydrophilic.

The topsheet 28 is preferably also accorded a mechanical treatment, such as "Clupaking" or "Micrexing" or the like, as was discussed above with respect to the backsheet 30, to enhance its softness and wearing comfort.

The preferred wet laid apertured tissue can be produced on a paper machine according to the method described in U.S. Pat. No. 3,881,987, issued to Benz on May 6, 1975. Preferably, the drainage member described in the aforementioned Benz patent should comprise the foraminous members described in U.S. Pat. No. 4,514,345, issued to Johnson, et al. on Apr. 30, 1985. The disclosure of each of these patents is incorporated herein by reference. The embryonic fibrous webs as would be produced as described above can be further dried using any convenient drying means as would be known to those skilled in the paper making art. For example, press felts, thermal hoods, infrared radiation, blow-through dryers and Yankee drying drums, either used alone or in combination. A particularly preferred drying method uses a press felt and a Yankee drying drum in sequence.

The use of such a method can provide wet laid fibrous assemblies having a range of aperture densities and percent open area. As used herein, the term "aperture density" is intended to mean the number of apertures per square inch of fibrous assembly surface and the term "percent open area" is defined as that portion of the fibrous assembly surface that is not occupied by fibers expressed as a percentage. Preferably the aperture density is between about 9 apertures per square inch (1 aperture per square centimeter) and about 400 apertures per square inch (62 apertures per square centimeter). More preferably the aperture density is between about 20 apertures per square inch (3 apertures per square centimeter) and about 111 apertures per square inch (17 apertures per square centimeter). The preferred apertured wet laid fibrous assemblies of the present invention preferably have a percent open area between about 20 percent and about 50 percent. More preferably the percent open area is between about 30 percent and about 40 percent. A particularly preferred wet laid fibrous assembly has an aperture density of about 81 apertures per square inch (6 apertures per square centimeter) with about 36 percent open area.

The tissue furnish further comprises a temporary wet strength resin. Such a temporary wet strength resin helps the topsheet 28 maintain its mechanical integrity during use of the interlabial absorbent structure 20 yet does not interfere with the dispersibility of the topsheet when the used interlabial absorbent structure 20 is flushed. Suitable temporary wet strength resins are the glyoxalated polyacrylamide resins available from Cytec Industries Inc. of Stanford, Conn. under the designation Parez™. Particularly preferred is Parez™ 631 NC. When Parez™ 631 NC is used at a level between about 0.5% and about 1.0% in the wet laid apertured tissue, the topsheet 28 has a satisfactory balance of mechanical integrity during use and dispersibility during disposal.

This preferred tissue is further provided with a multiplicity of fibrils 54 or "hairs" on the nonapertured portion of its body facing surface. These fibrils 54 reduce the surface wetness characteristics of the topsheet 28 by separating the wearer's body from any bodily fluids that may remain on the cellulosic body surface of the topsheet 28A. Table 3 compares the surface wetness characteristics of the topsheet 28 to the nonwoven topsheet used on a commercially available interlabial absorbent structure (KOTEX® OVERNITES from Kimberly Clark Corp. Neenah, Wis.). A method for measuring surface wetness is provided in the TEST METHODS section below.

TABLE 3

| Topsheet No. | 1 | 2 |
|---|---|---|
| Topsheet Type | Present Invention | Nonwoven |
| Resinous Coating Material | CA-105 | None |
| Fibril Density | 4500 fibrils/in$^2$ | N/A |
| Surface Wetness | 0.39 g | 0.49 g |

As can be seen in Table 3, the preferred topsheet of the present invention has somewhat improved surface wetness when compared to a typical nonwoven topsheet. The fibrils 54 also provide the body surface 28A with a pleasant, velour-like tactile feel.

The fibrils 54 preferably comprise the same water resistant resinous material used to coat the backsheet 30 to render it impermeable to bodily fluids (CA-105). The fibril density can vary between about 500 fibrils per square inch (77 fibrils per square centimeter) to about 11,000 fibrils per square inch (1700 fibrils per square centimeter). Preferably, the fibril density is between about 3000 fibrils per square inch (450 fibrils per square centimeter) and about 5000 fibrils per square inch (775 fibrils per square centimeter). Fibril length can vary between about 0.003 inches (0.07 mm) to about 0.04 inches (1.0 mm). Preferably, the fibril length is between about 0.004 inches (0.1 mm) and about 0.01 inch (0.3 mm). The Applicants have found that choice of fibril length and fibril density allows surface wetness and other topsheet characteristics, including the tactile feel, to be varied to achieve a desired balance of these characteristics.

Such fibrils 54 can be provided to the body surface 28A by the method described in co-pending, commonly assigned U.S. patent application Ser. No. 08/561,720 entitled "Fluid Pervious, Dispersible, and Flushable Webs Having Improved Functional Surface", filed on Nov. 22, 1995, in the names of Ahr, et al. the disclosure of which is incorporated herein by reference.

Alternatively, a wet laid apertured tissue produced according to the aforementioned U.S. Pat. No. 3,881,987 on a drainage member as described in the aforementioned U.S. Pat. No. 4,514,345 and having a wet strength resin incorporated therein may further comprise a garment surface 28B. The body surface 28A and the garment surface 28B are separated from one another by an intermediate portion 28C. The wet laid apertured tissue is treated to form a web such that the body surface of the web provides a structure which exhibits a surface energy less than the surface energy of the intermediate portion. In a preferred embodiment, the treated web exhibits a plurality of regions of comparatively low surface energy which define surface energy gradients where they interface with higher surface energy web surfaces. The Applicants have found that treating regions of the body surface 28A such that the difference in the work of adhesion for water between the treated regions and the remainder of the web is in the range of about 5 erg/cm$^2$ to about 145 erg/cm$^2$ increases in acquisition, dryness (i.e. reduces surface wetness) and masking characteristics may be obtained. For example, a silicone resin having a low surface energy can be applied to portions of the body surface 28A providing such regions of comparatively low surface energy. Webs having such surface energy gradients and work of adhesion are fully described in U.S. patent application Ser. No. 08/442,935, filed on May 31, 1995 in the name of Ouellette, et al. the disclosure of which is incorporated herein by reference.

In a preferred embodiment of the present invention, at least portions of the body surface 28A of the topsheet 28 are hydrophilic so as to help liquid to transfer through the topsheet faster than if the body surface was not hydrophilic. Such a hydrophilic surface helps to diminish the likelihood that bodily fluids will flow off the topsheet rather than flowing into and being absorbed by the absorbent core. In a preferred embodiment, surfactant is applied to the body surface 28A of the topsheet 28 (e.g. by extrusion coating or spraying) before the fibrils are printed thereon. Alternatively, the body surface of the topsheet can be made hydrophilic by treating it with a surfactant such as is described in the above referenced U.S. Pat. No. 4,950,254, the disclosure of which is incorporated herein by reference.

As shown in FIG. 6, the interlabial absorbent structure 20 is folded into a structure that is generally semi-oval when viewed from the side. The portion of the interlabial absorbent structure 20 that lies along the longitudinal centerline L will define a longitudinal ridge that will form the portion of the interlabial absorbent structure 20 that will be inserted furthest inward into the wearer's body (or "top" of the interlabial absorbent structure 20). When viewed from one of the ends, the interlabial absorbent structure 20 can be analogized to the shape of a tent having a top which forms the longitudinal ridge that defines the narrowest portion of the structure, and two sides. The longitudinal side edges will form the base of the tent-like structure, the portion which will be inserted the least distance into the wearer's body, and the widest portion of the structure. The longitudinal side edges 26 of the interlabial absorbent structure 20 may extend straight downward from the top of the folded structure. Alternatively, if the wearer's body dimensions are such that the longitudinal side edges 26 extend outward from the wearer's body and the wearer is wearing panties or other undergarments that contact the base of the structure, the longitudinal side edges 26 of the interlabial pad may contact the wearer's panties and fold slightly outward to form flap-like elements, F.

Figure 7:
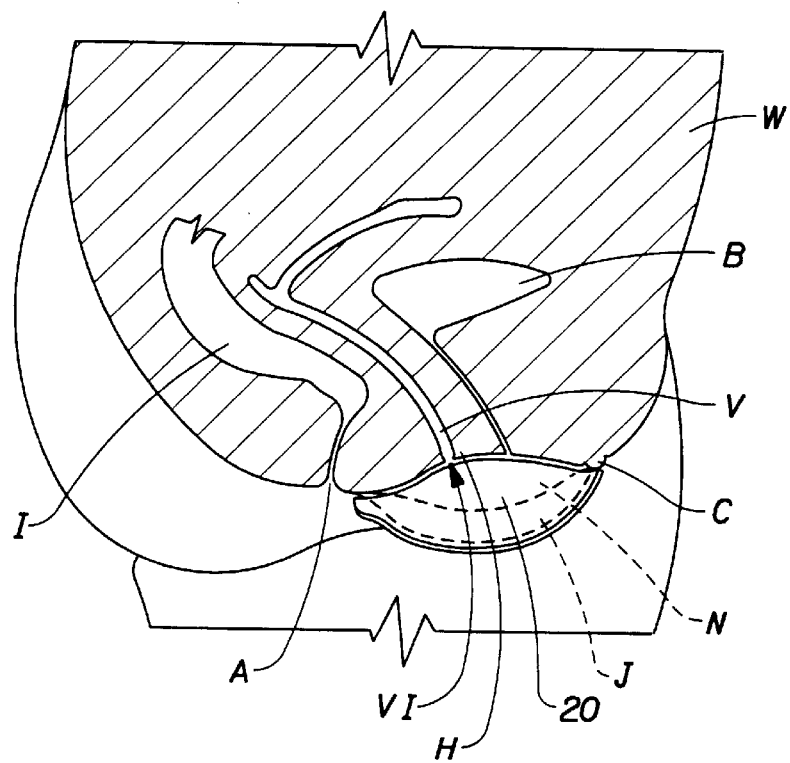
FIG. 7 is a cross section of a wearer showing the interlabial absorbent structure in place.

FIG. 7 shows the interlabial absorbent structure 20 in place in a wearer's body. The parts of the wearer's body, W, shown in FIG. 7 are designated as follows: bladder, B, clitoris, C, urethra, U, labia minora, N, labia majora, J, vagina, V, vaginal introitus, VI, anus, A, hymenal ring, H, and large intestine, I. As shown in FIG. 6, the interlabial absorbent structure 20 is folded along the longitudinal centerline L so that the two portions of the backsheet 30 on either side of the longitudinal centerline are brought adjacent to each other.

The interlabial absorbent structure 20 is inserted so that it is worn between the wearer's labia minora N and labia majora J and blocks the wearer's vaginal introitus VI without entering the vagina past the hymenal ring H. That is, the interlabial absorbent structure 20 lies at least partially in the vestibule bounded by the labia minora when such device is worn. The interlabial absorbent structure 20 may also cover, but does not necessarily occlude, the wearer's urethra U. Preferably, the interlabial absorbent structure 20 covers both the wearer's vaginal introitus VI and the wearer's urethra U. Ideally, the interlabial absorbent structure 20 is maintained in contact with as large a portion of the inner surface area of the wearer's labia minora N and labia majora J as possible. This will ensure that the interlabial absorbent structure 20 intercepts as much of the wearer's body exudates as possible. Preferably, the entire interlabial absorbent structure 20 is intended to be worn below the wearer's hymenal ring H.

The interlabial absorbent structure 20 may also contain a portion that is worn outside the wearer's labia majora J. This portion could, for example, be used for storage of body exudates that are transferred from the portion of the interlabial absorbent structure 20 that is worn between the wearer's labia minora and labia majora. The portion of the interlabial absorbent structure 20 that is worn between the wearer's labia minora and labia majora will, as a result, will have exudates drained therefrom, and be able to receive additional loadings of body exudates.

Optional Components

The Secondary Topsheet

The topsheet 28 may further comprise a secondary topsheet layer 29, as is shown most clearly in FIG. 2. Such a secondary topsheet layer is preferably conformable and non-irritating to the skin. When used, the secondary topsheet layer 29 is disposed between the primary layer of the topsheet 28 and the absorbent core 32 and joined to at least one of them. Suitable materials for the secondary topsheet layer 29 include, but are not limited to any of those materials used in the absorbent core such as tissue paper, creped cellulose wadding, cross-linked cellulose fibers, capillary channel fibers, absorbent foams, synthetic staple fibers, polymeric fibers. Preferably, the secondary topsheet layer 29 comprises a wet laid tissue paper. More preferably, such a secondary topsheet layer 29 is also be readily dispersible under the mild agitation conditions encountered when a conventional toilet is flushed. The above-mentioned DST 2 is a wet laid tissue that is readily dispersible in water and, as such, is suitable for use as a secondary topsheet layer 29. The secondary topsheet layer 29 provides additional structural stability to the interlabial absorbent structure 20 when such structures become wet with bodily fluids, such as menses or urine. Further, the secondary topsheet layer 29 may provide additional containment for any particulate superabsorbent polymers or absorbent gelling materials that may be in the absorbent core 32.

The Adhesive Portion

The interlabial absorbent structure 20 may also be provided with an adhesive portion for retention against a wearer's vaginal vestibule. As shown most clearly in FIGS. 1 and 2, topsheet 28 may be coated with a body adhesive 25. Preferably, such an adhesive holds the interlabial absorbent structure in close proximity to the vaginal vestibule throughout the full range of wearer movements, yet releases from the wearer's body when the interlabial absorbent structure 20 is exposed to the fluid pressure caused by normal urination. Such release allows the interlabial absorbent structure 20 to be expelled at urination reducing the inconvenience of changing. Suitable adhesives include pressure-sensitive, hydrophilic hydrogel adhesive materials, such as are disclosed in U.S. Pat. No. 5,336,208, issued to Rosenbluth, et al. on Aug. 9, 1994, the disclosure of which is incorporated herein by reference.

Assembly of the Interlabial Absorbent Structure

The topsheet 28 and the backsheet 30 are positioned adjacent the body surface 28A and the garment surface 28B, respectively, of the absorbent core 32 and are preferably joined thereto and to each other by attachment means (not shown) such as those well known in the art. For example, the backsheet 30 and/or the topsheet 28 may be secured to the absorbent core 32 or to each other by a uniform continuous layer of adhesive, a patterned layer of adhesive, or an array of separate lines, spirals, or spots of adhesive. In keeping with the objectives of the present invention, adhesives used in assembling the preferred interlabial absorbent structure 20 should be easily disrupted by the mild agitation conditions encountered when a conventional toilet is flushed. Adhesives which have been found to be satisfactory are the hot melt adhesive available from Findley Adhesives Inc. of Wauwatosa, Wis. under the designation H-9222-01 and the adhesive emulsion available from Air Products & Chemicals Corp. of Allentown, Pa. under the designation Airflex 401. Such adhesives may be applied by gravure printing or adhesive sprays. Also suitable is adhesive application by means of an open pattern network of filaments comprising several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference.

As noted above and shown in FIGS. 1 and 2, in the preferred embodiment of the interlabial absorbent structure 20 the topsheet 28 and the backsheet 30 each have length and width dimensions generally larger than those of the absorbent core 32 (i.e., the topsheet 28 and the backsheet 30 extend beyond the edges of the absorbent core 32). In the preferred embodiment of the interlabial absorbent structure 20 shown in FIGS. 1 and 2 the topsheet 28 and the backsheet 30 are joined to each other at least around the periphery 21 in an area of peripheral bonding 27 to form a wrapper which completely encloses the absorbent core 32. As used herein the term "area of peripheral bonding" is defined by those portions of the topsheet 28 and the backsheet 30 that extend beyond the absorbent core 32. As further noted above, the preferred topsheet 28 is disposed such that the body surface thereof 28A is that surface provided with a multiplicity of fibrils (that is, the fibrils comprise a portion of the outer surface of the interlabial absorbent structure 20), and the preferred backsheet 30 is disposed such that body surface 30A is provided with a moisture resistant resinous coating (that is, the moisture resistant resinous coating is disposed on at least the interior of the interlabial absorbent structure 20).

In keeping with the objects of the present invention, the topsheet 28 and the backsheet 30 are joined in the area of peripheral bonding 27 by means that are easily disrupted by the mild agitation conditions encountered when a conventional toilet is flushed. Means known to those skilled in the absorbent products art can be used to join the topsheet 28 and the backsheet 30 in the area of peripheral bonding 27 as long as such means do not interfere with the dispersibility of the interlabial absorbent structure 20. Suitable means for joining the topsheet 28 and the backsheet 30 in the area of peripheral bonding 27 are substantially the same as those suitable for joining the topsheet 28 and/or the backsheet 30 to the absorbent core 32. Preferably, the topsheet 28 and the backsheet 30 are joined using a water soluble adhesive (shown as 24 in FIGS. 1 and 2). Suitable adhesives include the hot melt adhesive available from Findley Adhesives Inc. of Wauwatosa, Wis. under the designation H-9222-01. A preferred water soluble adhesive 24 is the adhesive emulsion which is available from Air Products & Chemicals Corp. of Allentown, Pa. as Airflex 401.

Depending on the form of the adhesive, the water soluble adhesive can be applied to the interlabial absorbent structure 20 by means known to the art. For example, gravure coating, slot extrusion, and spray coating, particularly when the adhesive is applied as filaments swirled into a spiral pattern are all suitable. When used with the preferred water soluble adhesive emulsion Airflex 401 described above, gravure coating is particularly preferred.

As also noted above, the absorbent core 32 can be joined to one or both of the topsheet 28 and the backsheet 30 using a suitable water soluble adhesive 24. In the preferred embodiment of the present invention, the interlabial absorbent structure 20, both the topsheet 28 and the backsheet 30 are joined to the absorbent core 32 using the preferred water soluble adhesive emulsion Airflex 401.

If desired, the body adhesive 25 may also be applied to portions of the body surface 28A adjacent the periphery 21 using means known to those skilled in the art, such as printing.

When a interlabial absorbent structure 20 of the present invention is assembled as described above, it will readily disperse when exposed to the mild agitation conditions encountered when a conventional toilet is flushed. For example, when such interlabial absorbent structures are evaluated for flushability using the High Loading Protocol described in the TEST METHODS section below they flush in substantially the same manner as a commercially available toilet tissue ((CHARMIN®). These results can be explained by the following model:

1) The water soluble adhesive 24 joining the topsheet, the absorbent core and the backsheet rapidly dissolves allowing the components of the interlabial absorbent structure 20 to separate.
2) This separation exposes protected portions of these components to the water with a resulting decrease in the mechanical strength of these components.
3) The components further disperse into smaller particles that pass through the test apparatus similarly to a toilet tissue (CHARMIN®) control.

Various alternative embodiments of the interlabial absorbent structure of the present invention and the method of making the same are possible. For example, many other suitable components and arrangement of these can also be used in the interlabial absorbent structure. For example, the topsheet 28 could comprise an apertured, air laid fibrous assembly and the backsheet 30 could comprise a carded nonwoven material. Such substrates for the topsheet and the backsheet would still be treated with a resinous material as described above to provide them with the requisite properties to enable their use as a topsheet or backsheet. Such structures would still be joined to the absorbent core 32 and to each other at least in an area of peripheral bonding 27 by means that are easily disrupted by the mild agitation conditions encountered when a conventional toilet is flushed. Joining these alternative components in such a manner still allows them to separate on disposal which minimizes the risk of toilet clogging.

TEST METHODS

Trouser Tear Strength

Overview

This test is intended to determine the force necessary to propagate a tear in a material when the tear has already been initiated. Trouser tear may be measured on a wet or dry basis.

Method

The method of ASTM Standard Method D 1938-85 was used with the following exceptions.

Apparatus
Tensile Tester: Instron Model 5564 available from Instron Corp. of Canton, Mass.
Spray Apparatus: For wet trouser tear strength measurement. A suitable spray apparatus is available from Continental Sprayers, Inc. of St. Peters, Mo. as a model T85N trigger sprayer.

Conditioning
For wet trouser tear strength measurement, cut and insert a dry, conditioned sample into the test apparatus according to ASTM D 1938-85 and then spray the sample with temperature conditioned water to evenly apply about 7 grams of distilled water (10 strokes of the sprayer) over the sample surface to insure sufficient water is available to fully saturate the sample (Depending on the specific absorbent capacity of the material being evaluated some experimentation may be necessary to determine the amount of water necessary to fully saturate the sample). Allow about 5 minutes or other desired time for absorption of the applied water and saturation of the sample Report
Report, in grams, the mean and standard deviation of the maximum load measured for each sample tested.

Burst Strength

Overview
The test specimen, held between annular clamps, is subjected to increasing force that is applied by a 0.625 inch diameter, polished stainless steel ball. The burst strength is that force that causes the sample to fail. Burst strength may be measured on wet or dry samples.

Apparatus
Burst Tester
Intelect-II-STD Tensile Test Instrument, Cat. No. 1451-24PGB or the Thwing-Albert Burst Tester are both suitable. Both instruments are available from Thwing-Albert Instrument Co., Philadelphia, Pa. The instruments must be equipped with a 2000 g load cell and, if wet burst measurements are to be made, the instruments must be equipped with a load cell shield and a front panel water shield.

Conditioned Room
Temperature and humidity should be controlled to remain within the following limits:
Temperature: 73°±3° F. (23° C.±2° C.)
Humidity: 50±2% Relative Humidity Paper Cutter
Scissors or other equivalent may be used Pan
For soaking wet burst samples, suitable to sample size Solution
Water for soaking wet burst samples should be equilibrated to the temperature of the conditioned room.

Timer
Appropriate for measuring soak time

Sample preparation
1) Cut the sample to a size appropriate for testing (minimum sample size 4.5 in (11 cm)×4.5 in (11 cm)). Prepare a minimum of five samples for each condition to be tested.
2) If wet burst measurements are to be made, place an appropriate number of cut samples into a pan filled with temperature-equilibrated water.

Equipment Setup

1) Set the burst tester up according to the manufacturer's instructions. If an Intelect-II-STD Tensile Test Instrument is to be used the following are appropriate:

Speed: 12.7 centimeters per minute

Break Sensitivity: 20 grams

Peak Load: 2000 grams

2) Calibrate the load cell according to the expected burst strength.

Measurement and Reporting

1) Operate the burst tester according to the manufacturer's instructions to obtain a burst strength measurement for each sample.

2) Record the burst strength for each sample and calculate an average and a standard deviation for the burst strength for each condition.

3) Report the average and standard deviation for each condition to the nearest gram.

Flushability

Overview

As noted above, the terms "flushable or flushability" are defined as a product's capacity to pass through typical commercially available household toilets and plumbing drainage systems without causing clogging or similar problems that can be directly associated with the physical characteristics of the product. More specifically, catamenial products are evaluated for flushability via relative ease of toilet bowl and trap evacuation and subsequent transport through a simulated plumbing system.

The test procedure is designed to simulate two days of normal toilet usage for a family of 4 (2 men, 2 women). The test employs a flushing sequence to simulate the following conditions: male urination visits, female urination visits (including post urinary drying with tissue), disposal of catamenial product with cleaning using tissue, and bowel movement visits. The amount of tissue to be used for each tissue flush is a normal loading of 2 strips of seven sheets, or the High Loading of 5 strips of seven sheets. The normal loading is based on consumer research regarding typical habits and practices and the high loading is 2.5 times the normal loading. The test is designed to simulate the conditions a product will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

Figure 8:
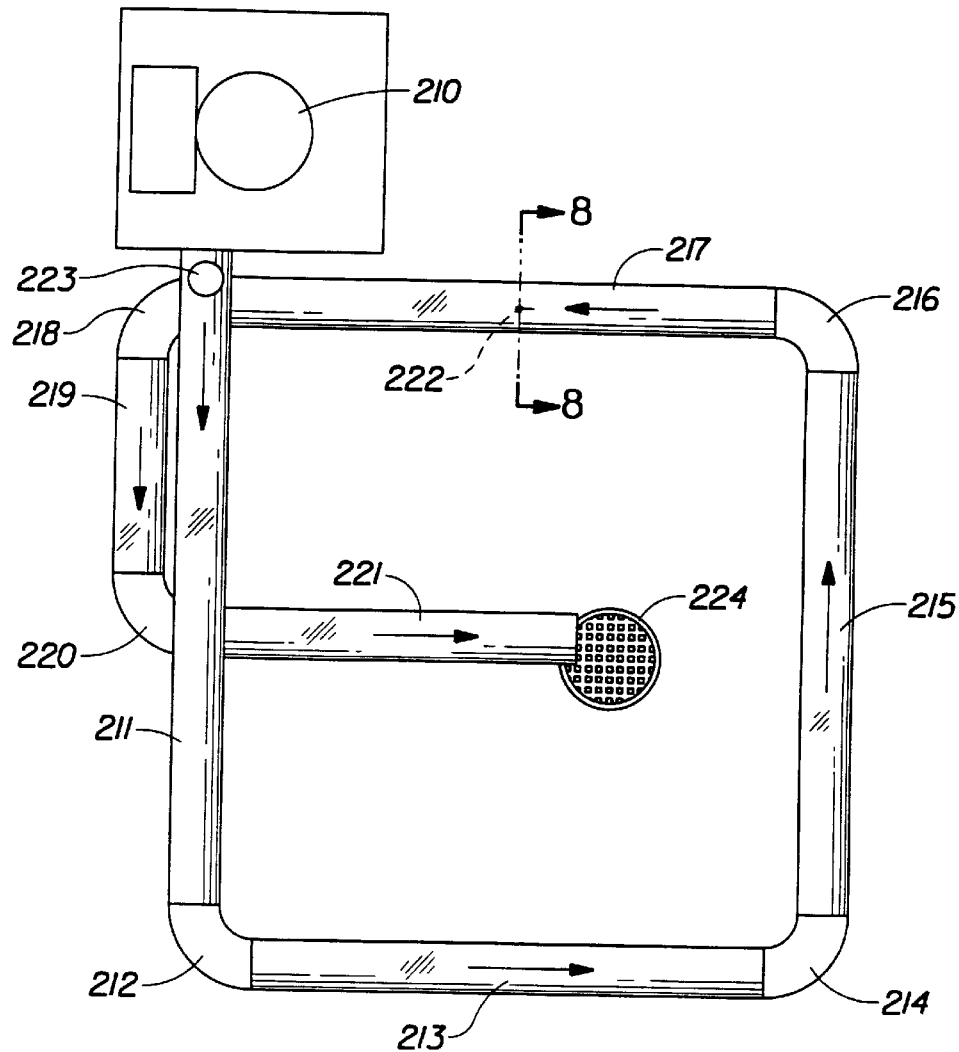
FIG. 8 plan view of an apparatus suitable for flushability determination according to the method described in the TEST METHODS section below.
Figure 9:
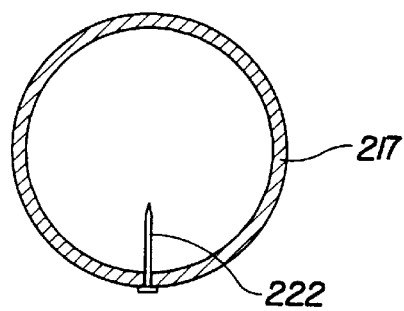
FIG. 9 is a cross section of the flushability apparatus of FIG. 8 taken along line 8—8 thereof.

An apparatus suitable for the flushability test is shown in plan view in FIG. 8. The apparatus includes:

a 3.5 gallon (13.2 liter) water saver siphon vortex toilet referred to as 210 (additional toilets can also be attached to the piping layout shown in FIG. 8 to evaluate the behavior of test samples using different flushing mechanisms such as commercial, pressure toilets);

approximately 59 feet (18 meters) of 4 inch (10 cm) id acrylic pipe (As can be seen from FIG. 8, the piping is assembled in roughly a square configuration having linear runs 211, 213, 215, 217, 219, 221 approximately 10 feet (3 meters) long);

a cast iron tee 223 slightly downstream of the toilet 210 that is open to the atmosphere for venting;

five cast iron ninety degree elbows 212, 214, 216, 218, and 220;

a snag 222 positioned vertically (FIG. 9) approximately 15 feet from the pipe's terminal end and approximately 1 inch (2.5 cm) long; and a screen (No. 4 Tyler sieve) to capture solid effluent for evaluation of disintegration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Control Tissue Product: CHARMIN®

Synthetic Fecal Material Prepared according to the method described below

Test Flushing Sequence

The test flushing sequence simulates 2 days of normal toilet usage for a family of 4 (2 men, 2 women; based on consumer habits and practices research). The sequence of 34 total flushes consists of 14 flushes with an empty bowl, 8 flushes with tissue only, 6 flushes with tissue and a catamenial product and 6 flushes with tissue and simulated fecal matter (SFM). When it is used, the SFM is placed in the bowl just prior to the addition of tissue. The SFM loading of 160 g±5 g consists of two 1 inch (2.5 centimeter)×4 inch (10 centimeter) pieces and one 1 inch (2.5 centimeter)×2 inch (5 centimeter) piece. Folded tissue strips (or the catamenial product) are placed in the bowl at 10 second intervals. Ten seconds after the final strip or pad is placed into the bowl, the toilet is flushed. The flushing sequence is described below as a series of two routines combined in the following order:

Routine#1 (To be performed 6 times for a total of 30 flushes)

1) Flush With Tissue Only—Take a drain line blockage reading 2 minutes after the water reaches the simulated obstruction, wait 1 additional minute, and move to step 2.

2) Flush With Empty Bowl. Take a drain line blockage reading 2 minutes after the water reaches the snag point and move to step 3.

3) Flush With Tissue and Pad—Take a drain line blockage reading 2 minutes after the water reaches the snag point, wait 1 additional minute, and move to step 4.

4) Flush With Empty Bowl. Take a drain line blockage reading 2 minutes after the water reaches the snag point and move to step 5.

5) Flush With Tissue and Simulated Fecal Mater (SFM). Take a drain line blockage reading 2 minutes after the water reaches the snag point, wait 1 additional minute.

Routine#2 (To be performed 1 time)

1) Flush With Tissue Only—Take a drain line blockage reading 2 minutes after the water reaches the snag point, wait 1 additional minute, and move to step 2.

2) Flush With Empty Bowl. Take a drain line blockage reading 2 minutes after the water reaches the snag point and move to step 3.

3) Flush With Tissue Only—Take a drain line blockage reading 2 minutes after the water reaches the snag point, wait 1 additional minute, and move to step 4.

4) Flush With Empty Bowl. Take a drain line blockage reading 2 minutes after the water reaches the snag point.

Total number of flushes per sequence is 34.

If, at any point in the flushing sequence, the product remains in the bowl or trap after flushing, the tissue and or pad is plunged into the drainage line manually and the flushing sequence will continue. After completion of each trial loading, the drainage pipe will be cleared prior to beginning subsequent testing.

The above described flushing sequence is repeated three times for each test product and three times for each control product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:
1) Incidence of failure to clear bowl and trap
2) Incidence of labored (difficult), but successful bowl and trap clearing
3) Incidence of product on simulated snag
4) Maximum level (%) of drain line blockage
5) Cumulative level (%) of drain line blockage over 2 days.

Preparation of Synthetic Fecal Material

I. Materials Needed

Feclone synthetic fecal matter (900 grams); (Available from Siliclone Studio, Valley Forge, Pa. as product BFPS-7 dry concentrate)

Tap water at 100° C. (6066 grams)

II. Equipment Needed

Mixer (Available from Hobart Corp., Troy, Ohio as Model A200)

Extruder (Available from Hobart Corp., Troy, Ohio as Model 4812)

Disposable Centrifuge tubes with screw caps (50 ml) (Available from VWR Scientific, Chicago, Ill. as Catalog No. 21-008-176)

Water Bath to control temperature to 37° C.

III. Preparation

1. Pour the 100° C. water into the mixing bowl of the mixer and add the dry Feclone concentrate.
2. Mix on low for 1 minute.
3. Mix on medium speed for 2 minutes.
4. After the material is well mixed, transfer to the extruder.
5. Using an ice pick, punch a small hole in the tip of each centrifuge tube.
6. Extrude the Feclone into the centrifuge tubes.
7. Cap the centrifuge tubes and store in the refrigerator.
8. Before using, put the tubes in the water bath at 38° C.

Hydrostatic Head

Overview

The height of a column of water over a sample of material that can be supported with no visual evidence of fluid transport through the sample.

Apparatus

Conditioned Room

Figure 10:
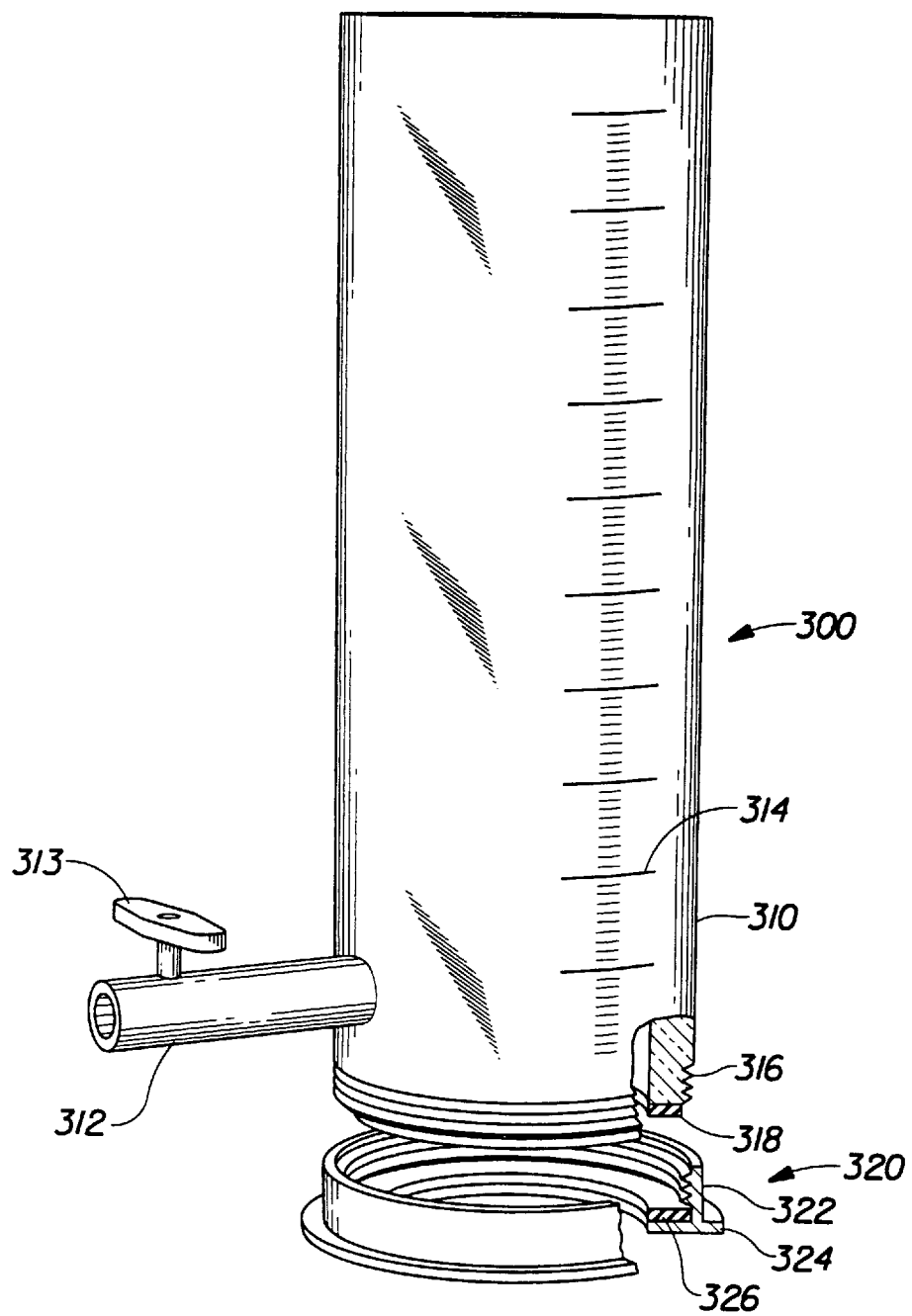
FIG. 10 perspective view showing the assembly of the apparatus used to measure hydrostatic head.

Temperature and humidity should be controlled to remain within the following limits:
Temperature: 73°±3° F. (23° C.±2° C.)
Humidity: 50±2% Relative Humidity Test Apparatus The test apparatus is shown in FIG. 10 and comprises:
a water vessel 300 which comprises:
1. a glass tube 2.125 inch (0.84 cm) diameter identified as 310;
2. a supply tube 312 adapted to deliver water (source not shown) at a controlled rate into the glass tube 310;
3. on/off valve 313 for controlling whether water is delivered to the water vessel 300;
4. indicia 314 scribed into the surface of the glass tube 310 adapted to allow measurement of the hydrostatic head to an accuracy of ±1 centimeter;
5. a male fitting 316 adapted to receive the sample holder 320; and
6. an annular rubber gasket 318 positioned beneath the lower end of the glass tube 310; and a sample holder 320 which comprises:
1. a female fitting 322;
2. an annular sample support 324 joined to the lower edge of the female fitting 322; and
3. an annular rubber gasket 326.

Ring Stand and Clamp

For holding the test apparatus in a vertical position

Mirror

Placed beneath the sample holder 320 to aid in seeing water penetration of the sample Method 1. Assemble the apparatus, using a ring stand and clamp to hold the water vessel 300 in a vertical orientation and connecting an adjustable water source to the supply tube 312.
2. Adjust the water temperature to 73° F.±2° F. (23° C.±1° C.).
3. Insert a water impervious blank (e.g., polyethylene film) into the sample holder 320, screw the sample holder 320 onto the water vessel 300, open the on/off valve 313, adjust the water flow (adjustment means not shown in FIG. 10) so the hydrostatic head rises at a rate of 1 inch per minute±0.1 inch per minute (2.5 centimeters per minute±0.25 centimeters per minute), and close the on/off valve 313.
4. Die cut a circular sample 2.625 inches in diameter and insert the sample into the sample holder 320. For backsheet samples of the preferred embodiment of the present invention the surface that has been provided with the water resistant resin should be placed facing upward. (The sample should be placed in the conditioned room at least 2 hours prior to testing.).
5. Screw the sample holder 320 onto the water vessel 300 being careful not to crease the sample. Tighten the sample holder only enough to insure that there are no leaks around the sample.
6. Place the mirror under the sample holder 320.
7. Start the water flow into the water vessel 300 by opening the on/off valve 313.
8. Observe the exposed surface of the sample by watching the mirror. Signs of water penetration include beading and spreading of a visible color change on the bottom surface of the sample.
9. Record the height of the column of water when penetration is first observed as the hydrostatic head for the sample.
10. Repeat the measurement 5 times and report the average and standard deviation of the measurements.

Surface Wetness

Overview

Surface wetness is a test designed to measure the amount of liquid which emerges from an absorbent structure, such as the interlabial absorbent structure 20 shown in FIG. 1, through a topsheet to cause wetness on the surface of the topsheet. The amount of moisture drawn through the topsheet is termed "surface wetness" and serves as an estimate of how dry the wearer's skin would remain if placed in contact with the absorbent structure.

Method

The test comprises wetting a 4 inch (10 centimeter)×4 inch (10 centimeter) sample of a topsheet material while superposed, body surface 28A facing up, on a standardized absorbent element preferably comprising a layer of airlaid comminuted wood pulp fibers enveloped between a pair of wet strength tissue plies with a simulated urine solution (available from Jayco Pharmaceuticals, Mehcanicsburg, Pa.). The simulated urine solution (4.0±0.3 ml) is delivered to the surface of the sample using a syringe pump. A uniform pressure loading of 0.25 psi (1.7 kPa) is applied to each sample while the simulated urine is being delivered so that the fluid is uniformly distributed throughout the sample. After all of the simulated urine has been delivered, the wetted sample is allowed to sit undisturbed for 5±0.5 minutes. The sample is covered with polyethylene film to minimize evaporation while the sample is sitting. The pressure is momentarily removed. A preweighed sample of filter paper (7 plies) approximately 5 inches (12 centimeters)×5 inches (12 centimeters) is inserted over the uppermost surface of the topsheet of the absorbent sample (Suitable filter paper is available from Ahlstrom Filtration Company of Mt. Holly springs, Pa. as Paper No 632). Sufficient weight to apply a predetermined pressure loading of 0.5 psi (3.4 kPa) is applied to the sample for a period of 15±1 seconds and removed. The filter paper is then removed and reweighed The amount of fluid absorbed by the filter paper is termed the "surface wetness" of the sample. Results are expressed in grams of fluid absorbed by the filter paper. As should thus be apparent, a lower "surface wetness" number is indicative of dryer surface feel.

Critical Surface Tension

The method described in TAPPI (Technical Association of the Pulp and Paper Industry) method T 698 pm-83, "Determination of Wetting Tension of Polyethylene and Polypropylene Films (modified visking analytical technique)" was used substantially as described therein with the exception that a commercially available series of known surface tension liquids (available from Corotec Corporation, Collinsville, Conn.) was used instead of the mixtures described in the TAPPI method and brushes, as supplied with the Corotec series were used instead of the cotton swabs.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. A water dispersible and flushable interlabial absorbent structure, said interlabial absorbent structure having a body surface at least a portion of which is in contact with the interior of the wearer's labia majora when worn, said interlabial absorbent structure comprising:
   a liquid pervious topsheet having a body surface;
   a dispersible, liquid impervious backsheet disposed beneath said topsheet; and
   an absorbent core disposed between said topsheet and said backsheet wherein said topsheet and said backsheet are joined using a water soluble adhesive in at least an area of peripheral bonding to encapsulate said absorbent core therebetween.

2. An absorbent structure according to claim 1 wherein said topsheet comprises a first fibrous assembly.

3. An absorbent structure according to claim 2 wherein said first fibrous assembly is a wet laid tissue and further comprises a wet strength resin.

4. An absorbent structure according to claim 3 wherein said temporary wet strength resin comprises a glyoxalated polyacrylamide resin.

5. An absorbent structure according to claim 2 wherein said first fibrous assembly is apertured.

6. An absorbent structure according to claim 2 wherein portions of said body surface of said topsheet have been provided with a first resinous material.

7. An absorbent structure according to claim 6 wherein said first resinous material comprises fibrils of a water resistant resinous material.

8. An absorbent structure according to claim 7 wherein said fibrils are provided at a density of between about 3000 fibrils per square inch and about 5000 fibrils per square inch.

9. An absorbent structure according to claim 6 wherein said first resinous material causes a difference in work of adhesion for water on said portions and the work of adhesion for water on the remainder of said body surface of between about 5 and about 145 ergs per square centimeter.

10. An absorbent structure according to claim 9 wherein said first resinous material comprises a silicone resin.

11. An absorbent structure according to claim 1 wherein said backsheet comprises a second fibrous assembly.

12. An absorbent structure according to claim 11 wherein said second fibrous assembly is a wet laid tissue and further comprises a wet strength resin.

13. An absorbent structure according to claim 11 wherein said second fibrous assembly has been coated on at least one surface with a second resinous material, said second resinous material causing said backsheet to become water resistant.

14. An absorbent structure according to claim 13 wherein said backsheet has a body surface and a garment surface and said second resinous material enables said backsheet to resist a hydrostatic head of at least about 15 cm and provides said body surface of said backsheet with a critical surface tension of greater than about 34 dynes per centimeter.

15. An absorbent structure according to claim 13 wherein said second resinous material is applied at a coating weight of between about 0.020 grams per square inch and about 0.25 grams per square inch.

16. An absorbent structure according to claim 1 wherein said topsheet comprises a first fibrous assembly and said backsheet comprises a second fibrous assembly.

17. An absorbent structure according to claim 16 wherein said first fibrous assembly comprises a first wet laid tissue and said second fibrous assembly comprises a second wet laid tissue.

18. An absorbent structure according to claim 1 wherein said absorbent core has a wet tear strength of less than about 60 grams.

19. An absorbent structure according to claim 1 wherein said absorbent structure delaminates into its components and said components disperse into fragments when said absorbent structure is immersed in water and the water is mildly agitated.

20. A water dispersible and flushable interlabial absorbent structure, said interlabial absorbent structure having a body surface at least a portion of which is in contact with the interior of the wearer's labia majora when worn, said interlabial absorbent structure comprising:

- a liquid pervious topsheet comprising a wet laid apertured tissue having a temporary wet strength resin incorporated therein wherein portions of a body surface of said topsheet have been provided with fibrils comprising a first resinous material;
- a dispersible, liquid impervious backsheet disposed beneath said topsheet, said backsheet comprising a wet laid tissue having a temporary wet strength resin incorporated therein, said wet laid tissue being coated on at least one surface with a second resinous material wherein said second resinous material causes said backsheet to become water resistant; and
- an absorbent core disposed between said topsheet and said backsheet wherein said topsheet and said backsheet are joined using a water soluble adhesive in at least an area of peripheral bonding to encapsulate said absorbent core therebetween.

21. An interlabial absorbent structure according to claim 20 wherein said fibrils are provided at a density of between about 3000 fibrils per square inch and about 5000 fibrils per square inch and said wet laid apertured tissue has between about 20 apertures per square inch and about 111 apertures per square inch therein.

22. An interlabial absorbent structure according to claim 20 wherein said second resinous material enables said backsheet to resist a hydrostatic head of at least about 15 cm and provides said body surface of said backsheet with a critical surface tension of greater than about 34 dynes per centimeter.

* * * * *